United States Patent
Schulz et al.

(10) Patent No.: US 8,357,824 B2
(45) Date of Patent: Jan. 22, 2013

(54) PROCESS FOR PREPARING NEOPENTYL GLYCOL BY CRACKING HIGH BOILERS OCCURRING IN THE PRODUCTION PROCESS

(75) Inventors: Rolf-Peter Schulz, Kriftel (DE); Horst Scholz, Dinslaken (DE); Thomas Hupperich, Schermbeck (DE); Peter Heymanns, Essen (DE); Tonia Weber, Darmstadt (DE); Alexander Kaufmann, Dinslaken (DE); Kurt Schalapski, Oberhausen (DE); Heinz Strutz, Moors (DE)

(73) Assignee: Oxea GmbH, Oberhausen (DE)

( * ) Notice: Subject to any disclaimer, the term of this patent is extended or adjusted under 35 U.S.C. 154(b) by 204 days.

(21) Appl. No.: 12/737,388

(22) PCT Filed: Jun. 25, 2009

(86) PCT No.: PCT/EP2009/004575
§ 371 (c)(1),
(2), (4) Date: Jan. 7, 2011

(87) PCT Pub. No.: WO2010/006688
PCT Pub. Date: Jan. 21, 2010

(65) Prior Publication Data
US 2011/0184212 A1  Jul. 28, 2011

(30) Foreign Application Priority Data

Jul. 15, 2008  (DE) .................. 10 2008 033 163

(51) Int. Cl.
*C07C 31/18* (2006.01)
(52) U.S. Cl. ........................................ 568/852
(58) Field of Classification Search .................. 568/852
See application file for complete search history.

(56) References Cited

U.S. PATENT DOCUMENTS

2008/0167506 A1  7/2008  Sirch et al. ............. 568/862

FOREIGN PATENT DOCUMENTS

| | | |
|---|---|---|
| DE | 12 69 605 B | 6/1968 |
| DE | 15 18 784 A1 | 8/1969 |
| DE | 199 48 112 A1 | 4/2001 |
| EP | 0 006 460 A1 | 1/1980 |

*Primary Examiner* — Sikarl Witherspoon
(74) *Attorney, Agent, or Firm* — Michael W. Ferrell

(57) ABSTRACT

The present invention relates to a process for obtaining neopentyl glycol by hydrogenating cracking of high-boilers occurring in the production process in the presence of copper-chromite catalysts. The hydrogenating cracking proceeds in the absence of solvent at a temperature of 140 to 220° C. and at pressures of 7 to 28 MPa.

28 Claims, No Drawings

PROCESS FOR PREPARING NEOPENTYL GLYCOL BY CRACKING HIGH BOILERS OCCURRING IN THE PRODUCTION PROCESS

CLAIM FOR PRIORITY

This substitute specification is submitted as a national phase entry of International Patent Application No. PCT/EP2009/004575 filed on Jun. 25, 2009 (International Publication No. WO 2010/000382), entitled "Process for Obtaining Neopentyl Glycol by Cracking High Boilers Occurring in the Production Process" ("Verfahren Zur Gewinnung von Neopentylglykol Durch Spaltung von im Herstellverfahren Anfallenden Hochsiedern") which claims priority to German Patent Application No. DE 10 2008 033 163.5 filed on Jul. 15, 2008. The priorities of International Patent Application No. PCT/EP2009/004575 and German Patent Application No. DE 10 2008 033 163.5 are hereby claimed and the referenced priority applications are incorporated herein in their entireties.

BACKGROUND OF THE INVENTION

The present invention relates to a process for obtaining neopentyl glycol by hydrogenative cracking in the presence of copper-chromite catalysts of high boilers formed in the production process.

Polyhydric alcohols or polyols are of considerable economic importance as condensation components for the formation of polyesters or polyurethanes, synthetic resin coatings, lubricants and plasticizers. Polyhydric alcohols obtained by a mixed aldol condensation of formaldehyde with isobutyraldehyde or n-butyraldehyde are of particular interest here. In the aldol condensation of formaldehyde with the appropriate butyraldehyde, an aldehydic intermediate is formed first and this subsequently has to be reduced to the polyhydric alcohol. An industrially important polyhydric alcohol which can be obtained by this process is neopentyl glycol [NPG, 2,2-dimethyl-1,3-propanediol] from the mixed aldolization of formaldehyde and isobutyraldehyde.

The aldol reaction is carried out using equimolar amounts in the presence of basic catalysts, for example alkali metal hydroxides or aliphatic amines, and firstly gives the isolatable intermediate hydroxypivalaldehyde (HPA). This intermediate can subsequently be converted as described in DE 1 800 506 A1 by reaction with excess formaldehyde in a Cannizzaro reaction into neopentyl glycol with formation of one equivalent of a formate salt. However, the catalytic hydrogenation of hydroxypivalaldehyde in the gas or liquid phase over a metal catalyst is also employed in industry. Nickel catalysts as described in EP 0 278 106 A1 have been found to be suitable hydrogenation catalysts. Catalysts based on copper, zinc and zirconium are used in the hydrogenation step in the process of EP 0 484 800 A2. According to the teachings of EP 0 522 368 A1, the hydrogenation step can be carried out under particularly mild pressure and temperature conditions when using copper-chromite catalysts. According to U.S. Pat. No. 4,855,515 A1, manganese-doped copper-chromite catalysts are particularly useful as hydrogenation catalysts in the hydrogenation of the aldolization product from the reaction of formaldehyde with isobutyraldehyde.

The hydrogenation process known from EP 0 522 368 A1 is carried out in the presence of at least 20% by weight of a lower alcohol, with the amount indicated being based on the mixture of alcohol and aldolization product. This prior art likewise claims that not only hydroxypivalaldehyde but also its disproportionation product formed by the Tishchenko reaction, viz. 2,2-dimethyl-1,3-propanediol monohydroxypivalate (HPN), is dissociated under the reaction conditions into neopentyl glycol.

Regardless of whether neopentyl glycol is prepared by the Cannizzaro process or the hydrogenation process, a series of secondary components which can be regarded as derivatives of neopentyl glycol are formed in the aldolization step. Owing to the high reactivity of formaldehyde and of isobutyraldehyde and also because of the high functionality of the products formed, e.g. hydroxyaldehydes and polyhydric alcohols, a series of secondary reactions such as the Tishchenko reaction, acetalization or ester formation can occur and lead to the formation of high boilers.

In the case of the reaction of formaldehyde with isobutyraldehyde, the high boilers are, inter alia, the following compounds:

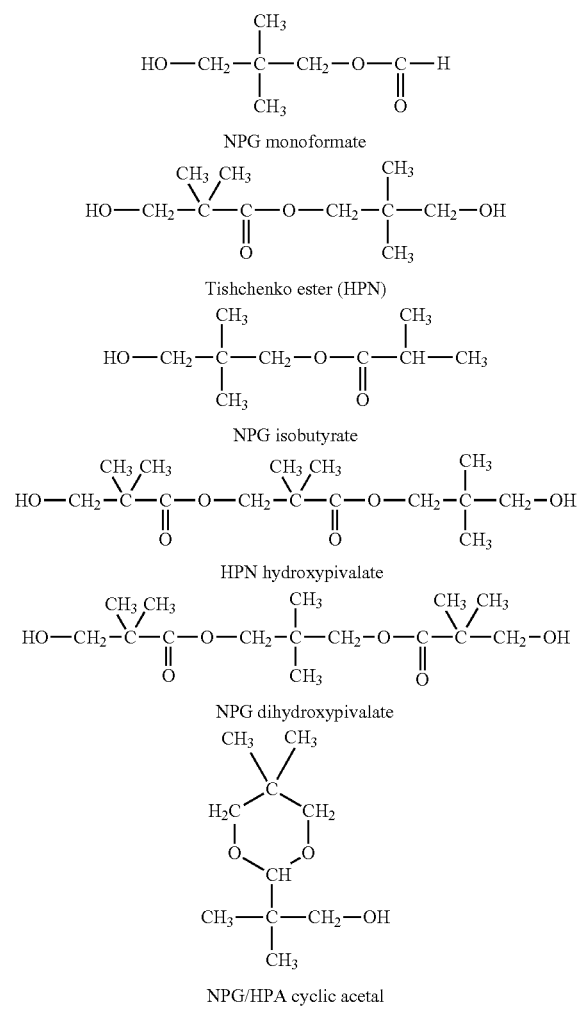

Oxygen-containing compounds such as relatively high-boiling esters or acetals are thus present in the high boilers from the preparation of neopentyl glycol.

The high boilers can be discharged from the production process at various points, for example after the aldolization step as bottom product from a vaporizer preceding the hydrogenation step, with the crude aldolization product taken off at the top of the vaporizer being hydrogenated in the gas phase by means of hydrogen over a metal catalyst to give neopentyl glycol. High boilers are also obtained in the purification by distillation to give the desired neopentyl glycol, for example as bottom product in the final pure distillation column.

This formation of high boilers is undesirable since units of the polyhydric alcohol are chemically bound in the high boilers and the yield of the desired neopentyl glycol is significantly reduced. Likewise, considerable amounts of neopentyl glycol are physically entrained in the high boilers. Furthermore, traces of high boilers in the end product can also have an adverse effect on the use properties.

WO 97/01523 A1 discloses that the cyclic acetals formed in the preparation of neopentyl glycol by reaction with formaldehyde can be cracked by means of hydrogen in aqueous acidic solution or suspension in the presence of metal catalysts at elevated temperature and elevated pressure to give the corresponding diols and formaldehyde. The formaldehyde liberated is hydrogenated to methanol under the reaction conditions.

According to the teachings of DE 1 518 784 A1, the high boilers obtained in the purification of the hydrogenation product in the final pure distillation column in the preparation of neopentyl glycol are at least partly recirculated to the hydrogenation reactor, with the crude aldolization product to be hydrogenated containing an excess of isobutyraldehyde in the known mode of operation. The catalytic hydrogenation of the crude aldolization product is carried out in the presence of copper-chromite catalysts.

EP 0 006 460 A1 discloses a process for preparing pure neopentyl glycol from crude hydroxypivalaldehyde containing, inter alia, the monoisobutyric ester of neopentyl glycol. According to the known process, the crude hydroxypivalaldehyde is hydrogenated in two stages in the presence of a barium-activated copper chromite catalyst.

It is known from US 2008/0167506 A1 that isobutyraldehyde can be reacted with formaldehyde in the presence of a tertiary amine to form hydroxypivalaldehyde which is subsequently hydrogenated in the presence of a copper catalyst which optionally contains chromium. The known process can be carried out with or without an organic solvent.

DETAILED DESCRIPTION OF THE INVENTION

The invention is described in detail below by reference to various examples and embodiments. Such discussion is for purposes of illustration only. Modifications to particular examples and embodiments within the spirit and scope of the present invention, set forth in the accompanying claims will be readily apparent to one of skill in the art.

Terminology used herein is given its ordinary meaning unless otherwise stated herein.

The known processes for obtaining neopentyl glycol from the high boilers formed in its preparation requires either acid treatment and addition of water with subsequent hydrogenation or the presence of a solvent when these high boilers are recirculated to the hydrogenation step in which the crude aldolization product initially obtained is hydrogenated at the same time.

It has surprisingly been found that neopentyl glycol can be recovered in large amounts in a simple manner from the high boilers formed in its preparation if these high boilers are treated with hydrogen in the absence of solvents and in the presence of copper-chromite catalysts in a separate hydrogenation reactor and the cracking products obtained are worked up by distillation.

The present invention therefore provides a process for obtaining neopentyl glycol from the high boilers formed in the reaction of formaldehyde with isobutyraldehyde. In this process, the high boilers are separated off from the process for preparing neopentyl glycol and treated in the liquid phase with hydrogen in the absence of solvent and in the presence of a copper-chromite catalyst at a temperature of from 140 to 200° C. and a pressure of from 7 to 28 MPa in a separate hydrogenation reactor and the cracking products obtained are worked up by distillation.

In contrast to the known processes in which the high boilers are recirculated to the hydrogenation step in which the crude aldolization product from the reaction of formaldehyde with isobutyraldehyde is hydrogenated at the same time, in the process of the invention the treatment with hydrogen, which can also be thought of as hydrogenative cracking of the high boilers, takes place in a separate hydrogenation reactor. This decoupled process configuration enables the reaction conditions for the hydrogenative cracking of the high boilers to be set in a targeted manner and independently of the reaction conditions to be selected in the hydrogenation of the crude aldolization product. Furthermore, carrying out the hydrogenative cracking in a separate hydrogenation reactor also allows the work-up of high boilers which are formed in the preparation and purification of neopentyl glycol by the Cannizzaro process in which the aldolization product is reacted with a further equivalent of formaldehyde and not hydrogenated by means of hydrogen.

The hydrogenative cracking of the high boilers is carried out in the absence of solvent. For the purposes of the present invention, "the absence of solvent" means that neither an organic solvent nor water is added in the treatment with hydrogen. However, small amounts of low-boiling compounds, for example isobutanol or n-butanol or water, which have solvent properties and are added or formed in preceding process steps can be present in the high boiler.

The high boilers formed in the preparation of neopentyl glycol (NPG) contain the abovementioned oxygen-containing compounds such as NPG monoformate, NPG isobutyrate, HPA Tishchenko ester, NPG/HPA cyclic acetal, NPG diisobutyrate and NPG dihydroxypivalate and also further esters, ethers and acetal compounds. The content of HPA Tishchenko ester and NPG dihydroxypivalate is particularly high. The high boilers also contain substantial amounts of neopentyl glycol and hydroxypivalaldehyde.

The high boilers to be used for the hydrogenative cracking can be separated off from the process for preparing neopentyl glycol at various process stages. They can then be introduced separately or in combined form into the hydrogenative cracking step to be carried out separately so as to obtain the desired polyhydric alcohol. In the preparation of neopentyl glycol, high boilers are, for example, obtained as bottoms from a vaporizer which precedes the hydrogenation of the crude aldolization product. Further high boilers can be discharged in the purification by distillation of the crude neopentyl glycol obtained after hydrogenation to give purified product. The combined high boiler streams from the preparation of neopentyl glycol can then be hydrogenated by the process of the invention.

The hydrogenative cracking according to the process of the invention is carried out in the presence of commercial copper-chromite catalysts. Their suitability for the hydrogenative cracking of ester compounds is known from the general prior art (Ullmann's Encyclopedia of Industrial Chemistry, 5th edition, vol. 9, VCH-Verlag). Copper-chromite catalysts can, according to H. Adkin, Org. React. 8, 1954, 1-27, be described as an equimolar combination of copper oxide and copper chromite, although they do not necessarily contain copper chromite. Such hydrogenation catalysts are described, for example in DE 26 11 374 A1, DE 1 518 784 A1, U.S. Pat. No. 4,855,515 A1 or EP 0 522 368 A1. The copper-chromite catalysts frequently further comprise activators such as barium, cadmium, magnesium, manganese and/or a rare earth metal. The copper-chromite catalysts which are suitable for the process of the invention can be used either without support materials or with support materials, for example with kieselguhr, silica gel or aluminum oxide, as powder or in the form of pellets, stars, extrudates, rings or other particles having a relatively large surface area.

Manganese-doped copper-chromite catalysts are particularly suitable for the treatment with hydrogen according to the invention.

The treatment with hydrogen or the hydrogenative cracking of the high boilers is carried out at temperatures of from 140 to 200° C., preferably from 160 to 200° C., and pressures of from 7 to 28 MPa, preferably from 7 to 20 MPa, without addition of a solvent and without addition of water. The use of higher temperatures is not advisable since unselective dissociation of the polyhydric alcohols occurs to an increased extent. Although higher pressures have a positive effect on the hydrogenation performance of the copper-chromite catalyst with high selectivity to the desired polyhydric alcohol, working under high pressure also requires a high energy input in order to compress the gas being reacted to an appropriately high pressure.

The treatment with hydrogen according to the invention is carried out continuously or batchwise in the liquid phase over fixed-bed catalysts, for example in a downflow or upflow hydrogenation. In addition, the treatment with hydrogen can also be carried out using suspended catalysts. In the continuous mode of operation, a space velocity over the catalyst V/Vh, expressed in volume throughput per catalyst volume and time, of from 0.2 to 1.2 h$^{-1}$, preferably from 0.4 to 1 h$^{-1}$, has been found to be advantageous.

In the batchwise mode of operation, from 1 to 10% by weight, preferably from 2 to 6% by weight, based on the solvent-free starting material, of the above-described copper-chromite catalysts is used.

The cracking products taken off from the hydrogenation reactor are firstly introduced into a high-pressure separator and depressurized to atmospheric pressure. The cracking products are subsequently worked up to give purified neopentyl glycol by known distillation processes, for example by the procedure known from EP 0 278 106 A1. In a particular embodiment, the cracking products are firstly mixed with crude neopentyl glycol and the mixture is subsequently worked up by distillation.

Neopentyl glycol can be recovered in a yield of more than 80% by weight, based on high boiler input, from the high boilers used by means of the treatment with hydrogen according to the invention. The novel process is illustrated by the following examples, but is not restricted to these embodiments.

EXAMPLES 600 ml of a commercial copper-chromite catalyst in the form of 3×3 mm pellets were placed in a tube reactor. After pressure testing by means of nitrogen, the temperature was slowly increased to 180° C. with a stream of nitrogen flowing through the reactor in order to activate the catalyst. Hydrogen was gradually introduced into the stream of nitrogen until a hydrogen flow of 60 liters per hour had been reached at an unchanged flow of nitrogen. The catalyst was then activated under these conditions over a period of 5 hours.

After the activation of the catalyst, a hydrogen pressure and a reaction temperature as per the conditions in tables 1 and 2 were set in the tube reactor. At the offgas flow set in each case, the appropriate amount of a high boiler mixture from the preparation of neopentyl glycol was introduced continuously into the tube reactor and the offgas stream discharged was introduced into a high-pressure separator and discharged via a level control into an atmospheric pressure receiver. The cracking products were mixed with crude neopentyl glycol and the mixture was distilled to give purified neopentyl glycol.

Examples at Various Temperatures and Pressures:

High boiler material having the following composition from the preparation of neopentyl glycol was used for the hydrogenative cracking experiments (gas-chromatographic analysis, figures in percent):

| | |
|---|---|
| First runnings | 0.6 |
| HPA | 18.3 |
| NPG | 20.8 |
| NPG monoformate | 0.2 |
| NPG diformate | 0.2 |
| Intermediate fraction | 0.1 |
| NPG monoisobutyrate | 4.5 |
| Cyclic acetal {HPA/NPG} | 0.2 |
| HPA Tishchenko ester/NPG diisobutyrate (TE, NPG di-i-B) | 46.6 |
| Tails | 8.5 |

The results of the cracking experiments at various temperatures and pressures are summarized in the following tables.

TABLE 1

Hydrogenative cracking of the high boilers from the preparation of neopentyl glycol (NPG feed) at various temperatures

| Pressure | [MPa] | 8.0 | 8.0 | 8.0 | 8.0 |
|---|---|---|---|---|---|
| Cat. temperature | [° C.] | 180 | 185 | 190 | 200 |
| NPG feed | [g/h] | 324 | 299 | 323 | 336 |
| Offgas | [l/h] | 260 | 255 | 220 | 230 |
| GC analyses | | | | | |
| First runnings | % | 2.4 | 3.5 | 3.1 | 8.4 |
| i-Butanol | % | 4.4 | 6.3 | 12.8 | 18.9 |
| NPG | % | 83.8 | 81.8 | 79.7 | 68.5 |
| NPG mono-i-butyrate | % | 1.0 | 0.8 | 0.6 | 0.6 |
| TE + NPG di-i-B | % | 6.0 | 5.5 | 1.8 | 2.3 |
| Total high boilers | % | 2.4 | 2.1 | 2.0 | 1.3 |

As the variation of the temperature shows, an increase in the cracking temperature leads to a decrease in the NPG content in the hydrogenated product but at the same time an increase in the proportion of isobutanol and first runnings components. This series of analytical data indicates increased unselective dissociation of neopentyl glycol and hydroxypivalaldehyde Tishchenko ester/NPG diisobutyrate, forming, inter alia, isobutanol and first runnings components, when the temperature is increased.

TABLE 2

Hydrogenative cracking of the high boilers from the preparation of neopentyl glycol (NPG feed) at different pressures.

|  |  |  |  |  |  |  |  | Comparison |
|---|---|---|---|---|---|---|---|---|
| Pressure | [MPa] | 20.0 | 18.0 | 16.0 | 14.0 | 12.0 | 8.0 | 6.0 |
| Cat. temperature | [° C.] | 180 | 180 | 180 | 180 | 180 | 180 | 180 |
| NPG feed | [g/h] | 230 | 300 | 310 | 310 | 310 | 240 | 235 |
| Offgas | [l/h] | 260 | 270 | 280 | 230 | 230 | 250 | 280 |
| GC analyses |  |  |  |  |  |  |  |  |
| First runnings | % | 2.9 | 3.6 | 2.7 | 3.0 | 3.1 | 3.6 | 3.5 |
| i-Butanol | % | 4.2 | 4.1 | 4.8 | 4.4 | 3.9 | 5.6 | 6.2 |
| NPG | % | 91.9 | 90.0 | 88.8 | 87.8 | 85.7 | 83.7 | 78.2 |
| NPG mono-i-butyrate | % | 0.1 | 0.2 | 0.3 | 0.4 | 0.6 | 0.7 | 1.3 |
| TE + NPG di-i-B | % | 0.4 | 1.6 | 2.1 | 2.8 | 5.0 | 4.5 | 8.1 |
| Total high boilers | % | 0.5 | 0.5 | 1.3 | 1.6 | 1.7 | 1.9 | 2.7 |

The series of analytical data shows the pressure dependence of the cracking rate of the hydrogenation catalyst. At a pressure of 20 MPa, virtually complete cracking and hydrogenation of the Tishchenko ester and the NPG diisobutyrate to neopentyl glycol is achieved.

Hydrogenation Experiment with Subsequent Distillation:

The hydrogenative cracking of the high boiler having the abovementioned composition from the preparation of neopentyl glycol was carried out under the same apparatus conditions as in the previous experiments. The hydrogenative cracking was carried out at a pressure of 8 MPa and a temperature of 180° C. using a feed rate of 300 g/h of high boilers, corresponding to a space velocity over the catalyst V/Vh of $0.5\,h^{-1}$. The cracking products had the following composition determined by gas chromatography (in percent):

| First runnings (containing methanol, isobutanol) | 7.4 |
| HPA | 0.0 |
| NPG | 82.0 |
| NPG monoformate | 0.0 |
| NPG diformate | 0.0 |
| Intermediate fraction | 0.3 |
| NPG monoisobutyrate | 0.9 |
| Cyclic acetal {HPA/NPG} | 0.3 |
| HPA Tishchenko ester/NPG diisobutyrate | 6.2 |
| Tails | 2.9 |

Under these conditions, cracking proceeded at a conversion of 91%, based on the feed rate of high boilers, and a selectivity to neopentyl glycol of 97.1%, corresponding to a yield of neopentyl glycol of 89.0%.

The cracking product obtained was mixed with crude neopentyl glycol in a weight ratio of 1:10 and the mixture was subsequently worked up by distillation in a 40 plate column at atmospheric pressure and a reflux ratio of 1:1 to give purified neopentyl glycol. After the first fraction had been taken off at a temperature at the top in the range from 87 to 100° C. and a temperature at the bottom in the range from 100 to 125° C., purified neopentyl glycol was obtained at a temperature at the top of 210° C. and a temperature at the bottom in the range from 210 to 260° C. Feed mixture, purified neopentyl glycol and distillation residue had the following composition determined by gas chromatography (in percent):

|  | Feed mixture | NPG fraction | Residue |
|---|---|---|---|
| First runnings (containing methanol, isobutanol) | 19.7 | 0.1 | 0.0 |
| HPA | 0.1 | 0.0 | 0.1 |
| NPG | 72.2 | 99.6 | 83.6 |
| Tri-n-propylamine | 6.0 | 0 | 0 |
| NPG monoformate | 0.0 | 0.0 | 0.0 |
| NPG diformate | 0.0 | 0.0 | 0.0 |
| Intermediate fraction | 0.1 | 0.0 | 0.4 |
| NPG monoisobutyrate | 0.5 | 0.2 | 3.8 |
| Cyclic acetal (HPA/NPG) | 0.1 | 0.1 | 0.4 |
| HPA Tishchenko ester/NPG diisobutyrate | 0.9 | 0.0 | 10.9 |
| Tails | 0.4 | 0.0 | 0.8 |

While the present invention has been described in conjunction with the specific embodiments and examples set forth above, many alternatives, modifications and variations thereof will be apparent to those of ordinary skill in the art. All such alternatives, modifications and variations are intended to fall within the spirit and scope of the present invention which is set forth in the claims of this case. In view of the foregoing discussion, relevant knowledge in the art and references discussed above in connection with the Background and Detailed Description, the disclosures of which are all incorporated herein by reference, further description is deemed unnecessary.

The invention claimed is:

1. A process for obtaining neopentyl glycol from the high boilers formed in the reaction of formaldehyde with isobutyraldehyde, characterized in that the high boilers are separated off from the process for preparing neopentyl glycol and treated in the liquid phase with hydrogen in the absence of solvent and in the presence of a copper-chromite catalyst at a temperature of from 140 to 200° C. and a pressure of from 7 to 28 MPa in a separate hydrogenation reactor and the cracking products obtained are worked up by distillation.

2. The process as claimed in claim 1, characterized in that the cracking products obtained are mixed with crude neopentyl glycol and the mixture is distilled to give purified neopentyl glycol.

3. The process as claimed in claim 1, characterized in that the copper-chromite catalyst further comprises barium, magnesium or manganese or a combination thereof as activator.

4. The process as claimed in claim 1, characterized in that the treatment with hydrogen is carried out at a temperature of from 160 to 200° C. and a pressure of from 7 to 20 MPa.

5. The process as claimed in claim 4, characterized in that the cracking products obtained are mixed with crude neopentyl glycol and the mixture is distilled to give purified neopentyl glycol.

6. The process as claimed in claim 4, characterized in that the copper-chromite catalyst further comprises barium, magnesium or manganese or a combination thereof as activator.

7. The process as claimed in claim 6, characterized in that the cracking products obtained are mixed with crude neopentyl glycol and the mixture is distilled to give purified neopentyl glycol.

8. In a process for preparing neopentyl glycol by reaction of formaldehyde with isobutyraldehyde and hydrogenation of the reaction products in a first reactor whereby high boilers are formed, the improvement comprising obtaining neopentyl glycol from the high boilers by:
   a.) separating the high boilers from said process for preparing neopentyl glycol; and
   b.) thereafter cracking and hydrogenating said high boilers in the liquid phase in the absence of solvent and in the presence of a copper-chromite catalyst at a temperature of from 140 to 200° C. and a pressure of from 7 to 28 MPa in a hydrogenation reactor separate from said first reactor; and
   c.) thereafter recovering neopentyl glycol obtained by cracking and hydrogenation of said high boilers.

9. The process as claimed in claim 8, characterized in that the products obtained by cracking and hydrogenation of said high boilers are mixed with crude neopentyl glycol and the mixture is distilled to give purified neopentyl glycol.

10. The process as claimed in claim 8, characterized in that the copper-chromite catalyst further comprises barium, magnesium or manganese or a combination thereof as activator.

11. The process as claimed in claim 8, characterized in that the treatment with hydrogen is carried out at a temperature of from 160 to 200° C. and a pressure of from 7 to 20 MPa.

12. The process as claimed in claim 11, characterized in that the products obtained by cracking and hydrogenation of said high boilers are mixed with crude neopentyl glycol and the mixture is distilled to give purified neopentyl glycol.

13. The process as claimed in claim 11, characterized in that the copper-chromite catalyst further comprises barium, magnesium or manganese or a combination thereof as activator.

14. The process as claimed in claim 13, characterized in that the products obtained by cracking and hydrogenation of said high boilers are mixed with crude neopentyl glycol and the mixture is distilled to give purified neopentyl glycol.

15. In a process for reacting formaldehyde with isobutyraldehyde in a first reactor wherein high boiling by-products are formed, the improvement comprising the steps of:
   a.) separating the reaction products into products enriched in said high boiling by-products and products depleted in said high boiling by-products;
   b.) cracking and hydrogenating said separated products enriched in high-boiling by-products in the liquid phase with hydrogen in the absence of solvent and in the presence of a copper-chromite catalyst at a temperature of from 140 to 200° C. and a pressure of from 7 to 28 MPa in a second reactor and thereby forming neopentyl glycol; and
   c.) thereafter recovering neopentyl glycol from the products obtained in step b.).

16. The process as claimed in claim 15, characterized in that the products obtained from step b.) are mixed with crude neopentyl glycol and the mixture is distilled to give purified neopentyl glycol.

17. The process as claimed in claim 15, characterized in that the copper-chromite catalyst further comprises barium, magnesium or manganese or a combination thereof as activator.

18. The process as claimed in claim 15, characterized in that the treatment with hydrogen is carried out at a temperature of from 160 to 200° C. and a pressure of from 7 to 20 MPa.

19. The process as claimed in claim 18, characterized in that the products obtained from step b.) are mixed with crude neopentyl glycol and the mixture is distilled to give purified neopentyl glycol.

20. The process as claimed in claim 18, characterized in that the copper-chromite catalyst further comprises barium, magnesium or manganese or a combination thereof as activator.

21. The process as claimed in claim 20, characterized in that the products obtained from step b.) are mixed with crude neopentyl glycol and the mixture is distilled to give purified neopentyl glycol.

22. In a process for producing neopentyl glycol by reacting formaldehyde with isobutyraldehyde in an aldolization reactor thereby forming hydroxypivalaldehyde and thereafter reducing said hydroxypivalaldehyde to neopentyl glycol in a reduction reactor, wherein by-products comprising high boiling acetals and esters are formed, the improvement comprising the steps of:
   a.) separating reaction products from at least one of said steps of reacting formaldehyde with isobutyraldehyde and reducing said hydroxypivalaldehyde to neopentyl glycol into products enriched in said high boiling by-products and products depleted in said high boiling by-products;
   b.) cracking and hydrogenating said products enriched in high-boiling by-products in the liquid phase with hydrogen in the absence of solvent and in the presence of a copper-chromite catalyst at a temperature of from 140 to 200° C. and a pressure of from 7 to 28 MPa in a reactor separate from both said aldolization reactor and said reduction reactor; and
   c.) distilling the products obtained from step b.).

23. The process as claimed in claim 22, characterized in that the products obtained from step b.) are mixed with crude neopentyl glycol and the mixture is distilled to give purified neopentyl glycol.

24. The process as claimed in claim 22, characterized in that the copper-chromite catalyst further comprises barium, magnesium or manganese or a combination thereof as activator.

25. The process as claimed in claim 22, characterized in that the treatment with hydrogen is carried out at a temperature of from 160 to 200° C. and a pressure of from 7 to 20 MPa.

26. The process as claimed in claim 25, characterized in that the products obtained from step b.) are mixed with crude neopentyl glycol and the mixture is distilled to give purified neopentyl glycol.

27. The process as claimed in claim 25, characterized in that the copper-chromite catalyst further comprises barium, magnesium or manganese or a combination thereof as activator.

28. The process as claimed in claim 27, characterized in that the products obtained from step b.) are mixed with crude neopentyl glycol and the mixture is distilled to give purified neopentyl glycol.

* * * * *